(12) United States Patent
Walsh

(10) Patent No.: US 8,926,552 B2
(45) Date of Patent: Jan. 6, 2015

(54) PARTICLE DELIVERY

(75) Inventor: Andrew James Lowenthal Walsh, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1056 days.

(21) Appl. No.: 12/540,087

(22) Filed: Aug. 12, 2009

(65) Prior Publication Data
US 2011/0040279 A1 Feb. 17, 2011

(51) Int. Cl.
*A61M 31/00* (2006.01)
*A61M 37/00* (2006.01)
*A61L 27/38* (2006.01)

(52) U.S. Cl.
CPC ........ *A61M 37/0069* (2013.01); *A61L 27/3834* (2013.01); *A61L 27/3856* (2013.01)
USPC .......................................................... 604/60

(58) Field of Classification Search
CPC ............ A61L 27/3834; A61L 27/3856; A61L 37/146; A61M 37/0069; A61I 37/146
USPC .................. 604/506, 60, 522, 57, 11, 13, 15; 424/532
See application file for complete search history.

(56) References Cited

U.S. PATENT DOCUMENTS

| | | |
|---|---|---|
| 5,906,934 A | 5/1999 | Grande |
| 6,440,098 B1 * | 8/2002 | Luscher .......................... 604/57 |
| 6,440,444 B2 | 8/2002 | Boyce |
| 6,497,875 B1 | 12/2002 | Sorrell |
| 6,610,026 B2 * | 8/2003 | Cragg et al. .................... 604/15 |
| 6,752,831 B2 | 6/2004 | Sybert |
| 7,338,657 B2 | 3/2008 | Vogel |
| 7,520,888 B2 | 4/2009 | Trieu |
| 2001/0051834 A1 | 12/2001 | Frondoza |
| 2004/0022864 A1 * | 2/2004 | Freyman et al. ............... 424/532 |
| 2004/0062753 A1 | 4/2004 | Rezania |
| 2004/0117033 A1 | 6/2004 | Frondoza |
| 2004/0197367 A1 | 10/2004 | Rezania |
| 2004/0241203 A1 | 12/2004 | Shakesheff |
| 2005/0071012 A1 | 3/2005 | Serhan |
| 2005/0147642 A1 | 7/2005 | Laredo |
| 2007/0292514 A1 | 12/2007 | Chan Pui et al. |
| 2008/0031858 A1 | 2/2008 | Chan et al. |

(Continued)

FOREIGN PATENT DOCUMENTS

| | | |
|---|---|---|
| WO | WO 98/28406 A1 | 7/1998 |
| WO | WO 2006/048783 A2 | 5/2006 |

(Continued)

*Primary Examiner* — Kami A Bosworth
*Assistant Examiner* — Imani Hayman
(74) *Attorney, Agent, or Firm* — Sorell, Lenna and Schmidt LLP

(57) ABSTRACT

A method for delivering particles to a target location of a subject includes slidably disposing a polymeric carrier in a lumen of a catheter. The lumen extends in the catheter from a proximal opening to a delivery region. The method further includes inserting the delivery region of the catheter in the target location of the subject and forcing the particles through the lumen of the catheter to cause the carrier and the particles to exit the delivery region of the catheter. The particles may be cells or drug-loaded microspheres. The carrier can serve to retain the particles in the target location for a period of time. For treatment of vertebral disc degeneration, the particles can be stem cells, the carrier can be formed from collagen, and the target location can be the nucleus pulposus.

10 Claims, 9 Drawing Sheets

(56) References Cited

U.S. PATENT DOCUMENTS

2008/0152691 A1* 6/2008 Drapeau et al. ............... 424/426
2008/0213228 A1  9/2008 Edinger
2009/0035855 A1  2/2009 Ying
2009/0076481 A1  3/2009 Stegmann
2013/0060338 A1* 3/2013 Hedrick et al. ............ 623/17.16

FOREIGN PATENT DOCUMENTS

| WO | WO 2007/084725 A2 | 7/2007 |
| WO | WO 2007/127790 A2 | 11/2007 |
| WO | WO 2008/082766 A2 | 7/2008 |
| WO | WO 2009/017267 A1 | 2/2009 |
| WO | WO 2009/036279 A1 | 3/2009 |

* cited by examiner

400 — Insert polymeric material into a lumen of a delivery element

410 — Force polymeric material out of delivery element by infusing fluid containing particles through lumen of delivery element 420 — Seed polymeric material with particles as particles are delivered

FIG. 6B

500 — Insert polymeric material into a lumen of a delivery element

510 — Fluidly couple lumen of delivery element to reservoir

520 — Insert distal portion of delivery element into subject at target location

530 — Deliver fluid containing particles from the reservoir to the target location through the lumen of the delivery element, causing the polymeric material to enter the target location

FIG. 7

PARTICLE DELIVERY

FIELD

The present disclosure relates to delivery of particles, such as microspheres or cells, to a subject.

BACKGROUND

Cells have been used or proposed for use in treating a variety of diseases. A variety of techniques have been developed for delivering cells to an appropriate area of a patient so that the cells can exert a therapeutic effect. However, in some circumstances, the cells are not readily retained in the appropriate area. For example, implantation of exogenous cells into intervertebral discs is an experimental therapeutic approach for treating chronic back pain associated with disc degeneration, but high pressures within the disc space may force the exogenous cells to exit the intervertebral space, e.g., along a track left by a cannula used to introduce the cells.

One way to address the cell retention issue is to seed the cells on a mesh or sponge material prior to introducing the cells into the patient, which can also provide a scaffold for cell growth. Depending on the size of the material, delivery of the cells may require invasive surgical methods. If the cell-seeded material is sufficiently small, a minimally invasive surgical procedure may be used. However, implantation of pre-seeded material requires multiple steps; namely, seeding and delivery. Each step can introduce variability into the procedure and can raise likelihood that the material will become contaminated or that the cell properties will change prior to implantation.

BRIEF SUMMARY

Among other things, the present disclosure describes minimally invasive methods and systems for use in delivering cells, or other particles, to a target location of a subject. In various embodiments, the systems and methods described herein provide for a simple procedure having minimal steps associated with delivery of cells or particles to a subject, while aiding in retention of the cells or particles in the target implant location.

In various embodiments, a method for delivering particles to a target location of a subject includes slidably disposing a polymeric carrier in a lumen of a delivery element. The lumen extends in the delivery element from a proximal opening to a delivery region. The method further includes inserting the delivery region of the delivery element in the target location of the subject and forcing the particles through the lumen of the delivery element to cause the carrier and the particles to exit the delivery region of the delivery element. The particles may be, for example, cells or drug-loaded microspheres. The carrier can serve to retain the particles in the target location for a period of time. In an embodiment for treatment of vertebral disc degeneration, the particles are stem cells, the carrier is formed from collagen, and the target location is the nucleus pulposus.

In various embodiments, a system includes an infusion apparatus having a reservoir configured to house particle-containing fluid. The system also includes a delivery element having a proximal end, a distal end, a delivery region between (which can be inclusive of) the proximal end and the distal end, and a lumen extending from the proximal end to the delivery region. The catheter is operably couplable to the infusion apparatus such that particles from the reservoir of the syringe are deliverable via the delivery region of the delivery element. The system also includes a polymeric carrier slidably disposed in the catheter. The system is configured such that delivery of the particles from the reservoir via the delivery region of the delivery element causes the polymeric carrier to exit to the delivery region of the delivery element. The carrier can interact with the particles within the delivery element or within the target location and retain the particles once delivered.

In some embodiments, a kit includes (i) a delivery element having a fluid delivery lumen, and (ii) a polymeric carrier slidably disposed in the lumen such that, when fluid is delivered via the lumen, the polymeric carrier is expelled from the lumen. The polymeric carrier may be inserted in the delivery element prior to use; e.g. by the manufacturer. The carrier may be simultaneously sterilized with the delivery element, allowing for packaging of delivery element having pre-inserted carrier.

Advantages of one or more of the various embodiments presented herein over prior articles, systems, or methods for delivering particles, such as microspheres or cells, to a subject will be readily understood from the following detailed descriptions when read in conjunction with the accompanying drawings

BRIEF DESCRIPTION OF THE DRAWINGS

FIGS. 6-7 are flow diagrams of embodiments of methods.

Figure 1A:
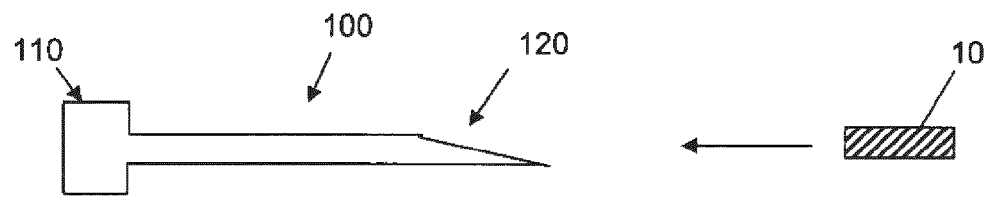
FIGS. 1A-B are schematic side views of a delivery element and polymeric carrier, with portions of the delivery element in FIG. 1B being transparent for purposes of illustration.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

It will be understood that spatial references, such as "horizontal," "vertical," "top," "inner," "outer," "bottom," "left," "right," "anterior," "posterior," "superior," "inferior," "upper," and "lower" are for illustrative purposes only and can be varied within the scope of the disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. Accordingly, a polymeric carrier "comprising" collagen may be a polymeric carrier "consisting essentially of", or "consisting of", collagen.

Among other things, the present disclosure describes minimally invasive methods and systems for use in delivering cells, or other particles, to a target location of a subject. In various embodiments, the systems and methods described herein provide for a simple procedure having minimal steps associated with delivery of cells, or other particles, to a subject, while aiding in retention of the cells in the target implant location.

Any particles may be delivered in accordance with the teachings presented herein. Preferably the particles adhere, attach, absorb, adsorb or the like to the polymeric carrier employed. The particles may be suspended in an appropriate fluid vehicle. In some embodiments, the particles to be delivered are cells.

Cells

A cell of any type may be delivered. For example, the cells may be connective tissue cells, epithelial cells, endothelial cells, hepatocytes, skeletal or smooth muscle cells, heart muscle cells, intestinal cells, kidney cells, or cells from other organs, stem cells, islet cells, blood vessel cells, lymphocytes, cancer cells, primary cells, cell lines, or the like. The cells may be mammalian cells, such as human cells, or may be derived from other origins. In numerous embodiments, the cells are stem cells which, as generally understood in the art, refer to cells that have the ability to continuously divide (self-renewal) and that are capable of differentiating into a diverse range of specialized cells. In some embodiments, the stem cells are multipotent, totipotent, or pluripotent stem cells that may be isolated from an organ or tissue of a subject. Such cells are capable of giving rise to a fully differentiated or mature cell types. A stem cell may be a bone marrow-derived stem cell, autologous or otherwise, a neuronal stem cell, a mesenchymal stem cell, a hematopoietic stem cell or an embryonic stem cell. A stem cell may be a multi-lineage cell derived from epithelial and adipose tissues, umbilical cord blood, liver, brain or other organ. In various embodiments, the stem cells are pluripotent stem cells, such as pluripotent embryonic stem cells isolated from a mammal. Suitable mammals may include rodents such as mice, rats, or primates including human and non-human primates.

Examples of human embryonic stem cell lines that have been established include, but are not limited to, H1, H7, H9, H13 or H14 (available from WiCell established by the University of Wisconsin) (Thompson (1998) *Science* 282:1145); hESBGN-01, hESBGN-02, hESBGN-03 (BresaGen, Inc., Athens, Ga.); HES-1, HES-2, HES-3, HES-4, HES-5, HES-6 (from ES Cell International, Inc., Singapore); HSF-1, HSF-6 (from University of California at San Francisco); I 3, I 3.2, I 3.3, I 4, I 6, I 6.2, J 3, J 3.2 (derived at the Technion-Israel Institute of Technology, Haifa, Israel); UCSF-1 and UCSF-2 (Genbacev et al., Fertil. Steril. 83(5):1517-29, 2005); lines HUES 1-17 (Cowan et al., NEJM 350(13):1353-56, 2004); and line ACT-14 (Klimanskaya et al., Lancet, 365(9471): 1636-41, 2005). Embryonic stem cells may also be obtained directly from primary embryonic tissue. Typically this is done using frozen in vitro fertilized eggs at the blastocyst stage, which would otherwise be discarded.

Other sources of pluripotent stem cells include induced primate pluripotent stem (iPS) cells. iPS cells refer to cells, obtained from a juvenile or adult mammal, such as a human, that are genetically modified, e.g., by transfection with one or more appropriate vectors, such that they are reprogrammed to attain the phenotype of a pluripotent stem cell such as an human embryonic stem cell. Phenotypic traits attained by these reprogrammed cells include morphology resembling stem cells isolated from a blastocyst as well as surface antigen expression, gene expression and telomerase activity resembling blastocyst derived embryonic stem cells. The iPS cells typically have the ability to differentiate into at least one cell type from each of the primary germ layers: ectoderm, endoderm and mesoderm. The iPS cells, like hESC, also form teratomas when injected into immuno-deficient mice, e.g., SCID mice. (Takahashi et al., (2007) Cell 131(5):861; Yu et al., (2007) Science 318:5858).

Prior to delivery to a subject, the cells may be suspended in a suitable medium, such as a buffered saline solution. One or more growth or other factors may be included with the suspended cells. The factors may facilitate cellular proliferation, adhesion, self-renewal, differentiation, or the like. Examples of factors that may be added to or included in the medium include muscle morphogenic factor (MMP), vascular endothelium growth factor (VEGF), interleukins, nerve growth factor (NGF), erythropoietin, platelet derived growth factor (PDGF), epidermal growth factor (EGF), activin A (ACT) such as activin A, hematopoietic growth factors, retinoic acid (RA), interferons, fibroblastic growth factors, such as basic fibroblast growth factor (bFGF), bone morphogenetic protein (BMP), peptide growth factors, heparin binding growth factor (HBGF), hepatocyte growth factor, tumor necrosis factors, insulin-like growth factors (IGF) I and II, transforming growth factors, such as transforming growth factor-$\beta1$ (TGF$\beta1$), and colony stimulating factors. One skilled in the art will appreciate that the factor(s) selected will vary depending on the cell type used and the outcome desired.

The cells may be suspended at any suitable concentration. In some embodiments, the cells are suspended at a concentration of between about $1\times10^5$ cells/ml to about $1\times10^9$ cells/ml.

Microparticles

In some embodiments, the particles to be delivered are microparticles, such as microcapsules or microspheres having an associated therapeutic agent. The microparticles may be made according to any suitable technique, such as described in, for example, (i) U.S. Pat. No. 4,384,975 to Fong, entitled "Process for preparation of microspheres", issued on May 24, 1983, (ii) U.S. Pat. No. 4,479,911 to Fong, entitled "Process for preparation of microspheres and modification of release rate of core material", issued on Oct. 30, 1984, (iii) U.S. Pat. No. 4,389,330 to Tice et al, entitled "microencapsulation process", issued on Jun. 21, 1983, (iv) U.S. Pat. No. 4,530,840 to Tice et al., entitled "Injectable, long-acting microparticle formulation for the delivery of anti-inflammatory agents, issued on Jul. 23, 1985, (v) U.S. Pat. No. 4,933,105 to Fong, entitled "Process for preparation of microspheres", issued on Jun. 12, 1990, (vi) U.S. Pat. No. 5,187,150 to Speiser et al, entitled "Polyester-based composition for the controlled release of polypeptide medicinal substances", issued on Feb. 16, 1993, (vii) U.S. Pat. No. 5,476,663 to Okada et al., entitled "Prolonged release microcapsule", issued on Dec. 19, 1995, (viii) U.S. Pat. No. 5,480,868 to Kamei et al., entitled "Sustained-release preparation", issued on Jan. 2, 1996, or (ix) U.S. Pat. No. 5,980,947 to Yamakawa et al., entitled "Process for producing drug-containing microspheres by oil-in-water evaporation process", issued on Nov. 11, 1999.

Any suitable therapeutic agent may be associated with the delivered microparticle. By way of example, an anti-inflammatory or analgesic agent is associated with a microparticle.

Examples of anti-inflammatory agent suitable for use in a human include steroids, such as cortisone, hydrocortisone, prednisone, dexamethasone, methyl-prednisilone, and derivatives thereof; and non-steroidal anti-inflammatory agents (NSAIDs). Non-limiting examples of NSAIDS include ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate.

Examples of analgesics that may be employed include local anesthetics, such as lidocaine, prilocaine, mepivicaine, benzocaine, bupivicaine, amethocaine, lignocaine, cocaine, cinchocaine, dibucaine, etidocaine, procaine, veratridine (selective c-fiber blocker) and articaine. It will be understood that some anti-inflammatory agents may also serve as analgesics.

Polymeric Carriers

Any suitable polymeric carrier may be delivered in accordance with the teachings presented herein. Preferably, the polymeric carrier is capable of interacting with the delivered particle to retain the particle in the target location of a subject for a period of time longer than if the carrier was not employed. For example, the particle may be able to attach, adhere, adsorb, absorb, or the like to the polymeric carrier. Examples of some polymeric materials that may be used to form a carrier include, but are not limited to, collagen, gelatin, hyaluronic acid, fibrin, albumin, keratin, silk, elastin, glycosaminoglycans (GAGs), polycaprolactone (PCL), polyethylene glycol (PEG), polyethylene oxide (PEO), polyvinyl alcohol (PVA) hydrogel, polyvinyl pyrrolidone (PVP), co-polymers of PVA and PVP, other polysaccharides, platelet-gel, peptides, carboxymethyl cellulose, and other modified starches and celluloses. Collagen includes but is not limited to collagen-based material, which may be autogenic, allogenic, xenogenic or of human-recombinant origin, such as the collagen-based material described in U.S. Patent Application Publication Nos. 2004/0054414 (naming Trieu and Sherman as inventors, entitled "Collagen-based materials and methods for augmenting intervertebral discs", published on Mar. 18, 2004) and 2004/0228901 (naming Trieu and Sherman as inventors, entitled "Collagen-based materials and methods for treating synovial joints", published on Nov. 18, 2004).

In some embodiments, it is desirable for the polymeric carrier to be compressible, formable, and readily hydratable. In various embodiments, the polymeric carrier has a water absorption of about 100% or more. Polymeric materials having such properties include collagen-containing materials.

In embodiments where the particles to be introduced are cells, it may be desirable for the polymeric carrier to serve as a scaffold for cell growth once the polymeric carrier and the cells are introduced into a subject. Polymeric carriers having properties capable of supporting cell attachment and growth include collagen-containing materials.

The polymeric carrier, in many embodiments, is a sponge, mesh, pad or strip of material that can be rolled, wadded, compressed, or the like, for insertion into a cannula. In some embodiments, the carrier can expand as it exits the cannula and becomes hydrated. In some embodiments, a therapeutic agent such as a drug or protein biologic is incorporated into or on the carrier.

Systems

Figure 1B:
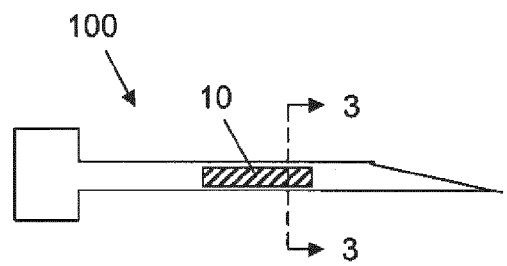
Figure 2A:
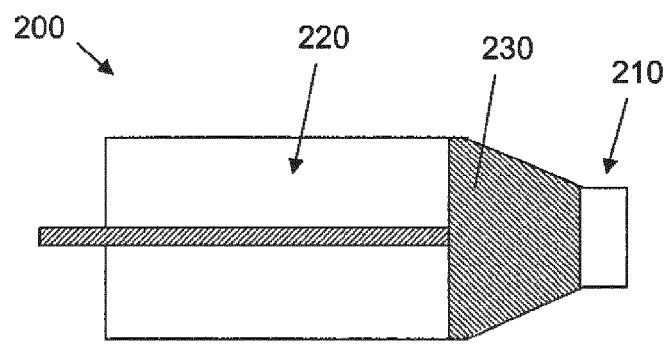
FIGS. 2A-D are schematic side views of a delivery system including a syringe and delivery element with portions being transparent for purposes of illustration.
Figure 2B:
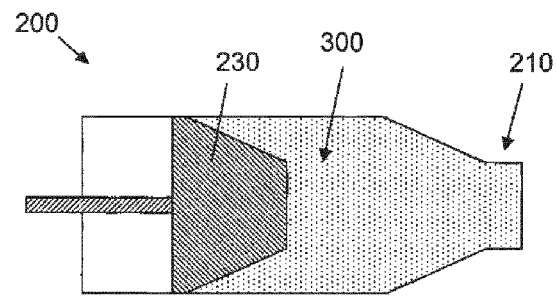
Figure 2C:
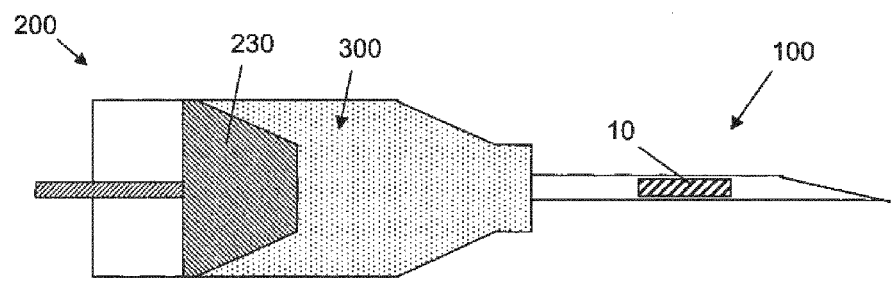
Figure 2D:
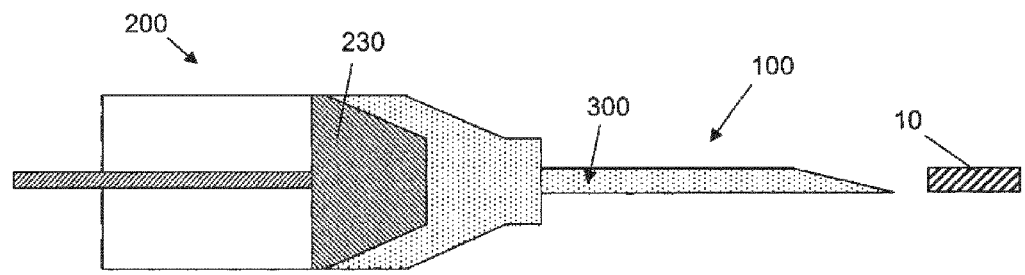
Figure 3:
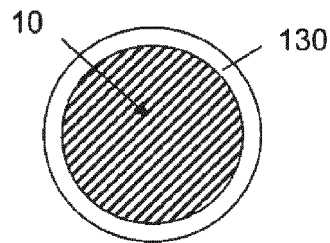
FIG. 3 is a schematic radial cross-section of the delivery element and polymeric carrier depicted in FIG. 1A taken along line 3-3.

Referring to FIGS. 1A-B and FIGS. 2A-D, an overview of an embodiment of a system that can be used to deliver particles, such as cells, and a polymeric carrier 10 to a subject is shown. The system includes a delivery element 100 having a distal portion 120 for inserting into a subject and a proximal portion 110 for coupling to a syringe 200 or other delivery device having a reservoir for housing fluid 300 containing the particles. The polymeric carrier 10 is inserted into a lumen of the delivery element 100, as schematically shown in FIG. 1B (see FIG. 3 for a radial cross-section of the polymeric carrier 10 inserted into a lumen defined by the body 130 of the cannula). The polymeric carrier 10 may be squeezed, rolled or compressed, as necessary or desired, to facilitate insertion into the lumen of the cannula 100. In some embodiments, the polymeric carrier 10 may be wetted, e.g. with water, to aid in squeezing or rolling, depending on the properties of the polymeric material. In the embodiments depicted in FIGS. 1-2, the delivery element 100 is operably couplable to a syringe 300 or delivery device. The delivery device 200 has distal end portion 210 configured to sealingly engage the proximal portion 110 of the delivery element. Any suitable connection mechanism may be employed to couple the proximal portion 110 of the delivery element 100 and the distal portion 210 of the delivery device 210. For example, the proximal portion 110 of the delivery element 100 and the distal portion 210 of the delivery device 210 may connect via quick release connection, such as snap fit or press fit, via luer lock connection, via screw engagement mechanism, or the like.

Prior to coupling the delivery element 100 to the syringe 200 or deliver device, fluid 300 may be introduced into the syringe 200 or delivery device. In the depicted embodiment, the syringe 200 includes a plunger 230 axially moveable within the syringe 200 to allow fluid to be draw into the reservoir 220 or expelled from the reservoir 220 of the syringe 200. In the embodiment depicted in FIG. 2A, the reservoir 220 contains no fluid for delivery to a subject, and the plunger 230 is fully advanced. In the embodiment shown in FIG. 2B, the plunger 230 is withdrawn and the reservoir 220 contains particle-containing fluid 300. A delivery element 100 with inserted polymeric carrier 10 is coupled to the syringe 200 (see, e.g., FIG. 2C), the plunger 230 is advanced, forcing fluid to exit the syringe 200 via the coupled delivery element 100 and causing the polymeric carrier 10 to exit the delivery element 100 (see, FIG. 2D).

In some embodiments, the delivery element 100 is permanently coupled or attached to the delivery device 200 (i.e., forms a permanent part of the delivery device), and the polymeric carrier 10 is inserted into the delivery element 100 while the delivery element is attached to the delivery device 200.

Any suitable syringe or delivery device may be employed. One example of a suitable delivery device is an Everest Disposable Inflation Device available from Medtronic, Inc. The Everest device is typically used for inflation of balloon catheters, but may be readily modified to deliver particle-containing fluid. Such a device allows for slow manual infusion of particle-containing fluid, which is desirable in situations where rapid infusion may cause the fluid to track in a retrograde fashion along the delivery element. Of course, the system employed may vary depending on the intended use. In some embodiments, the delivery device employs an automated delivery mechanism. In some embodiments, a delivery device having an active pumping mechanism, such as a peristaltic pump, a piston pump, a gas propelled pump, or the like, is employed. For example, a Harvard pump may be employed.

Any suitable delivery element may be employed. For example, the delivery element may be a catheter, cannula or needle. A catheter is a hollow, flexible tube configured to be inserted into a body cavity, duct, vessel, tissue, or the like for delivery of fluids, particles, devices, or the like. A cannula is a flexible tube, usually containing a trocar at one end, which is configured to be inserted into a bodily cavity, duct, vessel, or the like to deliver fluids, particles, devices, or the like. A needle is a slender, usually sharp-pointed instrument for puncturing tissue, which can be used for injecting fluids, particles, devices, or the like into a subject. In some embodiments, the delivery element is an 18 or higher gauge needle. Such needles, whether regular or thin-walled, tend to have a sufficient inner diameter to accept a polymeric material introduced manually, yet have a sufficiently small outer diameter for use in a variety of locations of a subject, such as introduction into an area of the subject's vertebral column.

In numerous embodiments, the polymeric material is inserted into the delivery element and packaged together. In such embodiments, the delivery element and inserted polymeric material may be sterilized in a single step, e.g. by steam, ethylene oxide, e-beam radiation, gamma radiation, or the like.

Figure 4A:
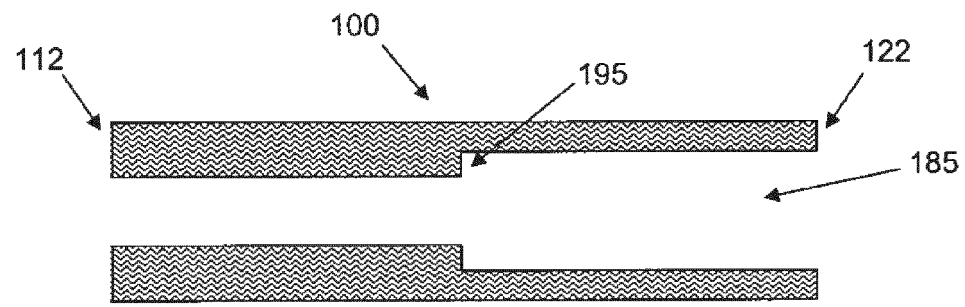
FIG. 4A is a schematic longitudinal section of an embodiment of a delivery element.
Figure 4B:
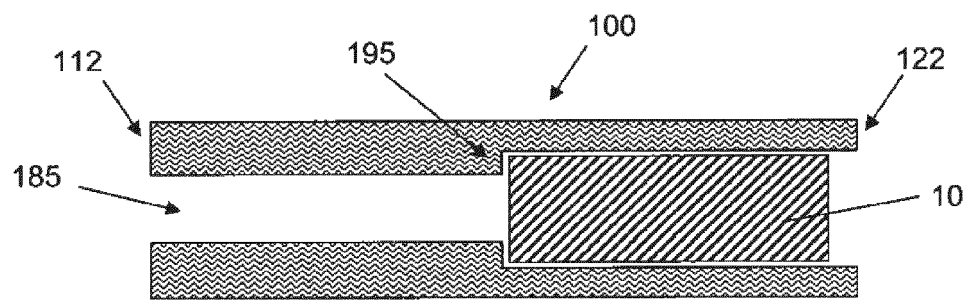
FIG. 4B is a schematic longitudinal section of a polymeric carrier disposed in the lumen of the delivery element depicted in FIG. 4A.

Referring now to FIGS. 4A-B, a delivery element may include a stop feature 195, such as the depicted shoulder, to prevent the polymeric material from being inserted to far into the lumen 185 of the delivery element 100. The stop feature 195 may project into the lumen 185 at any suitable location between the proximal end 112 and the distal end 122 of the delivery element 100, as shown. The stop feature 195 may also prevent aspiration of the polymeric material 10 into a syringe or delivery device to which the delivery element 100 by preventing proximal movement of the polymeric material 10 in lumen 185 beyond the stop feature 195. It will be understood that any suitable stop feature 195 other than the depicted shoulder may be employed.

Figure 5A:
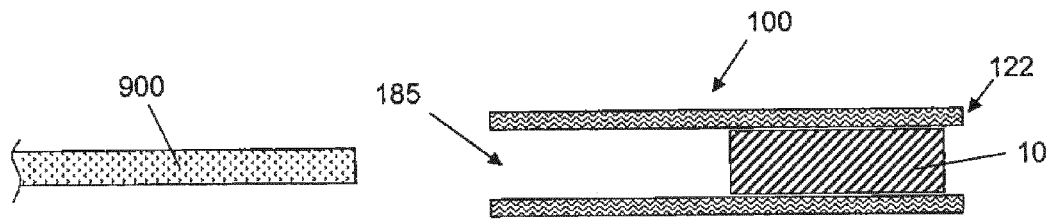
FIG. 5A is a schematic longitudinal section of a polymeric carrier disposed in the lumen of the delivery element and of a pushing element.
Figure 5B:
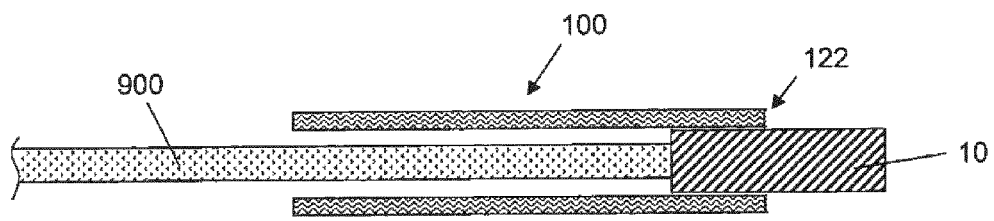
FIG. 5B is a schematic longitudinal section of a pushing element pushing a polymeric carrier out of the lumen of the delivery element.

Referring now to FIGS. 5A-B, a pushing element 900, such as a rod, stylet, or the like, may be inserted into the lumen 185 of the delivery element 100 to push the polymeric material 10 out of the delivery element 100 (e.g., beyond the distal end 122 as shown in the depicted embodiment). The pushing element 900 may be employed to push the polymeric material 10 out of the delivery element 100 after the particle containing fluid has been delivered via the delivery element 100 to ensure that the polymeric material 10 has been delivered (e.g., after the delivery element is uncoupled from the syringe or delivery device), before the particle containing fluid is delivered via the delivery element 100 (e.g., before the delivery element is coupled to the syringe or delivery device), or the like.

Methods

Figure 6A:
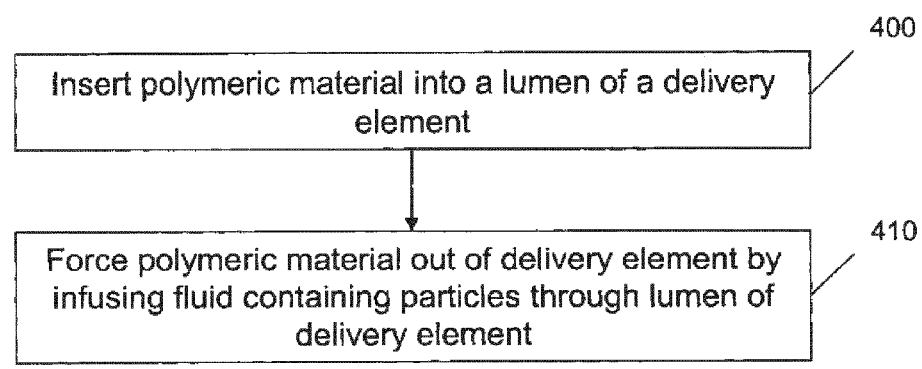

Referring to FIGS. 6-7 flow diagrams of representative methods are shown. As illustrated in FIG. 6A and as generally discussed above, a polymeric carrier can be inserted into a lumen of a delivery element (400) and the polymeric carrier can be forced out of the delivery element by infusing particle-containing fluid through the lumen of the catheter (410). If the particles of the fluid are capable of being adsorbed, absorbed, attached, adhered or otherwise interacting with the polymeric carrier, the polymeric carrier can be seeded with the particles as it is being forced out of the lumen and can continue to be further seeded after it has been expelled from the lumen as additional particle-containing fluid is delivered from the delivery element (420, FIG. 6B).

Referring now to FIG. 7, a polymeric carrier may be inserted into a lumen of a delivery element (500). The lumen of the delivery element may be fluidly coupled with a reservoir housing particle-containing fluid (510). The distal portion of the delivery element may be introduced into a subject at a target location (520), and the particle-containing fluid may be delivered from the reservoir to the target location through the lumen of the delivery element, causing the polymeric carrier to enter the target location (530). The polymeric carrier can serve to retain at least some of the particles at the target location for a period of time so that the particles may serve a therapeutic, diagnostic, investigational, or other purpose at the target location.

The systems and devices described herein may be used for a variety of purpose, such as to provide a therapy to a patient, to diagnose a condition of a patient, to monitor the well-being of a patient, to study the effects of particles (e.g., cells or microparticles) delivered to a particular location of a patient, to study surgical techniques employing polymeric material and particles, or the like. In addition, the systems and devices described herein may be used to deliver particles, and associated polymeric material, to a variety of target locations of a subject, whether in vivo, ex vivo, or in models. For the purposes of brevity, delivery to an area of a vertebral column is discussed below. However, it will be understood that particles may be delivered using systems and methods described herein to other areas of a subject. For example, particles may be delivered intrathecally, intraparenchymally, intracardially, etc.

Figure 8:
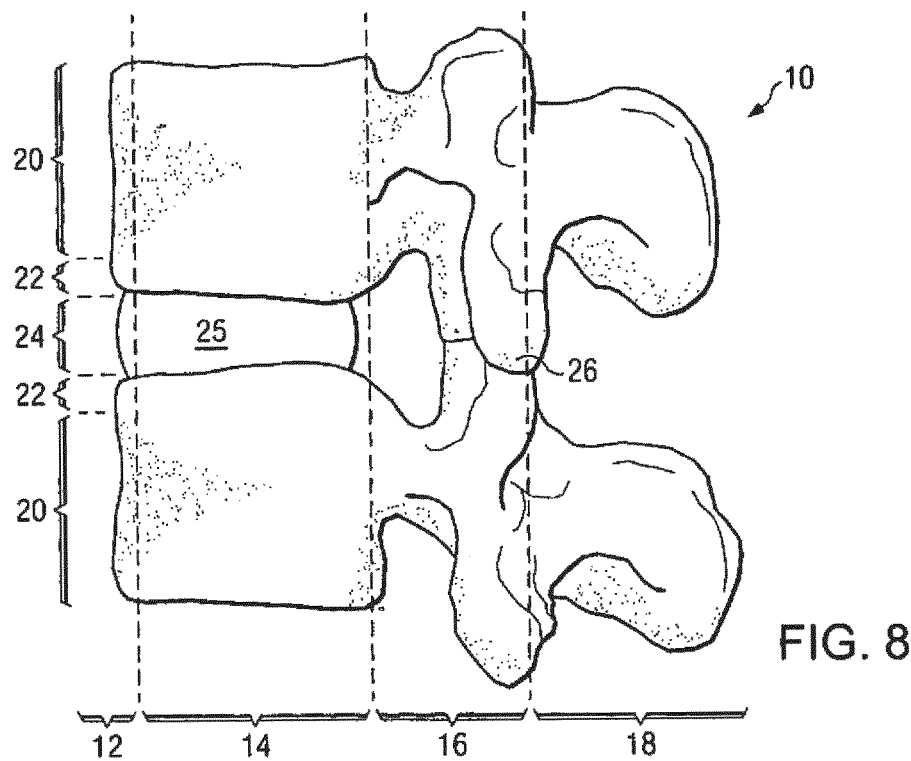
FIG. 8 is a schematic sagittal view of a motion segment of a vertebral column.
Figure 9:
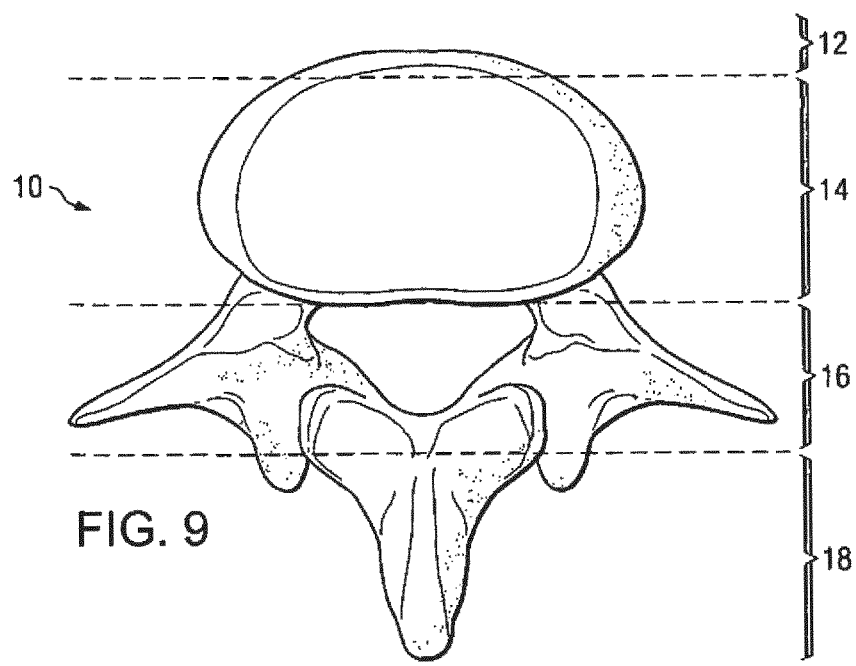
FIG. 9 is a schematic superior view of a vertebral body depicted in FIG. 6.

Referring now to FIGS. 8-9, the reference numeral 10 refers to a motion segment of a vertebral column. Motion segment 10 includes an intervertebral disc 25 and a facet joint 26. Motion segment 10 may be considered as having several regions extending from anterior to posterior. These regions include an anterior region 12, an anterior column region 14, a posterior region 16, and a spinous process region 18. The anterior column region 14 may be further considered to have several regions extending longitudinally along the column. These regions include a vertebral body region 20, an endplate region 22, and a disc space region 24. Disc space region 24 includes the nucleus and annulus forming intervertebral disc 25.

Particles and associated polymeric carrier may be delivered to any of the regions illustrated in FIGS. 8 and 9. In various embodiments, the particles are used to treat the vertebral column. For example, the particles may be used to repair or regenerate a degenerated area of the vertebral column, may be used to reduce or prevent degeneration of an area of the vertebral column, or may be used to treat a symptom, such as pain, of a disease associated with the vertebral column.

Figure 10:
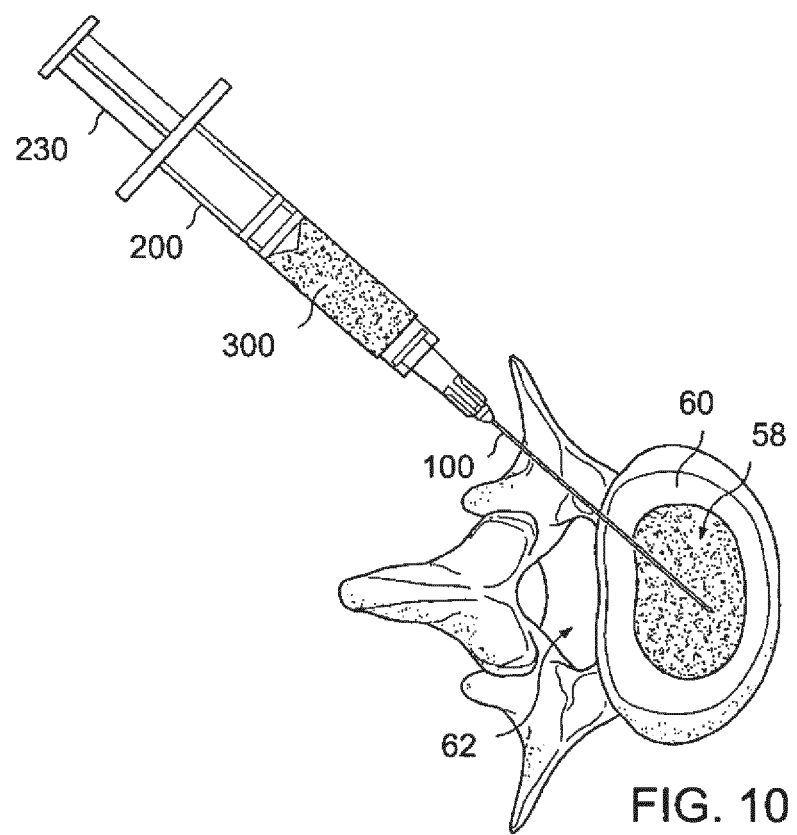
FIG. 10 is a schematic illustration of an embodiment of a method for delivering particles to a disc space in a vertebral column.

In some embodiments, disc degeneration is treated by introduction of stem cells, such as mesenchymal stem cells, into the nucleus pulposus. For example and with reference to FIG. 10, a particle-containing fluid 300 is shown poised for injection into the nucleus pulposus 58 contained within a disc annulus 60 in an intervertebral disc space 62. In the depicted embodiment, the fluid 300 is contained within a syringe 200 attached to a hypodermic needle 100. The needle 100 is inserted into the nucleus pulposus 58. Depression of the syringe plunger 230 will cause polymeric material (not shown) inserted into the needle 100 to enter the nucleus pulposus 58, along with the stem cell-containing fluid 300. The polymeric carrier serves to retain the stem cells within the nucleus pulposus 58 for a period of time.

Figure 11A:
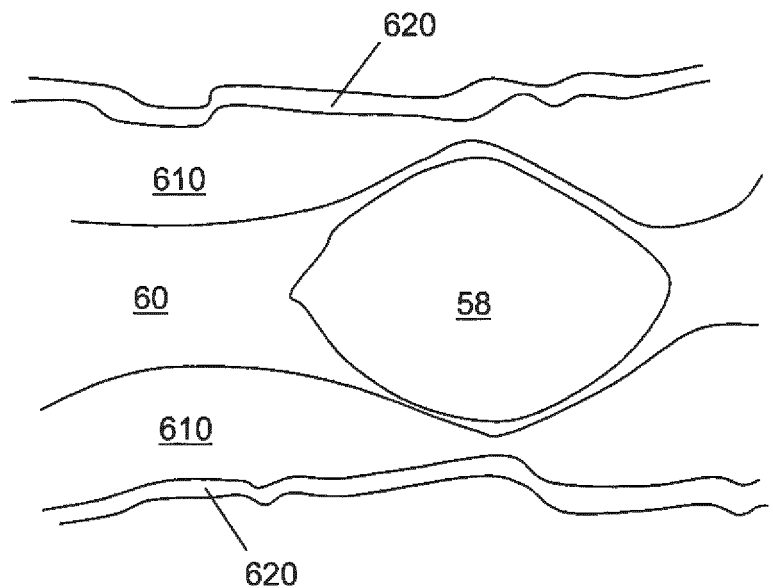
FIGS. 11A-D are schematic illustration of an embodiment of a method for delivering particles to a disc space in a vertebral column, with the vertebral column shown in a schematic saggital section.
Figure 11B:
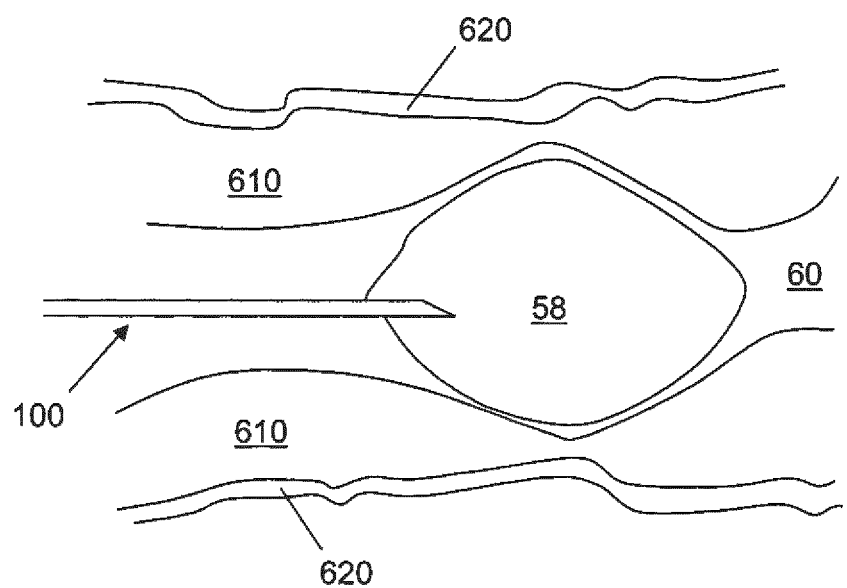
Figure 11C:
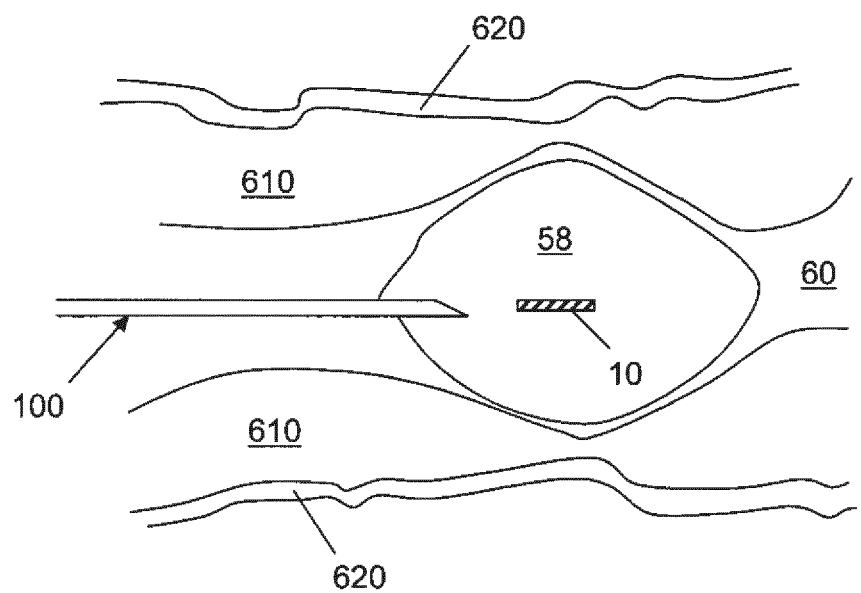
Figure 11D:
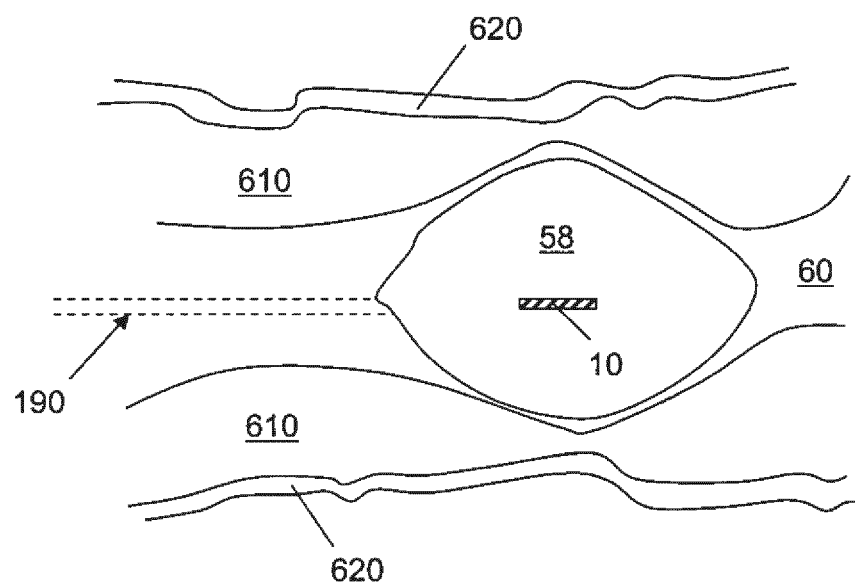

Referring now to FIGS. 11A-D, a schematic method for injecting stem cells into a nucleus pulposus 58 is shown (saggital section). Shown are the nucleus pulposus 58, annulus fibrosus 60, subchondral bone 610, and growth plates 620. As shown in FIGS. 11B-C, a delivery element 100 is inserted into the nucleus pulposus 58, and polymeric carrier 10 is expelled from the delivery element 100 into the nucleus pulposus 58 (due to pressure associated with delivery of stem-cell containing fluid (not shown) through needle 100). The delivery element 100 is then withdrawn, leaving a track 190, along which fluid may migrate. As the nucleus pulposus 58 is under a good deal of mechanical load, pressure may tend to force injected material out of the nucleus pulposus 58 via the track 190. The carrier 10 can serve to retain the particles associated with the carrier 10 in the nucleus pulposus for a longer period of time than if the particles were introduced without the carrier, as the carrier is less likely to be expelled from the nucleus pulposus than the particles alone.

When delivering stem cells for purposes of treating disc degeneration, it may be desirable to coadminister factors that promote chondrogenesis, such as TGFβ or bone morphogenic protein. Such factors can be delivered separately or in the same fluid as the cells. In some embodiments, the factors are loaded into or onto microparticles, such as microspheres or microcapsules, and delivered with the cells. In some embodiments, the factors are loaded into or onto the carrier.

In the following, non-limiting examples are presented, which describe various embodiments of the systems, devices, compositions and methods discussed above.

EXAMPLES

Example 1

Acute In Vitro and In Vivo Assessment of a Solid Carrier for Cell or Drug Delivery to Intervertebral Discs The success of cell or drug therapy to treat painful, degenerated intervertebral discs will depend, in part, on reliable delivery and retention of the therapeutic agents within the disc. The lack of vasculature in the disc favors that the agents be implanted directly into the disc space; e.g. via a needle or catheter. Damage from placing a needle into the disc and large internal pressures pose technical challenges to retention of therapeutic agents such as cells or drug-loaded microspheres. Combining cells or drug-loaded microspheres with biomaterials to serve as vehicles or scaffolds may enhance retention and efficiency.

In this study, solid material was evaluated acutely in vitro and in vivo for use as a delivery vehicle for stem cells or microspheres into intervertebral discs. Methods were established for delivering cells and microspheres into discs in combination with absorbable collagen sponge using an 18 gauge spinal needle. Acute cell retention and distribution of injected microspheres are described.

A. Absorbable Collagen Sponge (ACS)
A.1. In Vitro Analysis of Delivery into Porcine Discs
A method of delivering cells or microspheres with ACS through a spinal needle was developed through in vitro experimentation.

Materials:
1. Absorbable collagen sponge (Integra LifeSciences).
Methods:
A strip of collagen sponge was rolled between fingers into a smaller diameter that then fit inside an 18 gauge thin-walled needle. It was found that moistened gloved fingers worked better than gloved fingers that were not moistened.

In the first experiment, blue dye was filled into a 1 cc syringe and the syringe attached to the syringe gun. The 18 gauge needle with ACS inside was attached to the syringe, and inserted into a disc on a cadaveric spine. Fluid was dispensed from the syringe into the disc, which also pushed the collagen into the disc. The disc was cut open for observation.

In a second experiment, a saline solution containing 15 µm scarlet microspheres was loaded into a syringe in the syringe gun. A collagen pre-filled needle was placed on the syringe. The tip was placed into a 1.5% solution of alginate, a viscous substitute for nucleus pulposus, in a clear plastic vial. Solution was pushed through the needle and into the vial.

Results:
The first experiment demonstrated that the collagen sponge could be delivered through a needle and into the nucleus using fluid pressure. The collagen sorbed the injected blue dye.

The second experiment allowed visualization of the sorption process. As solution was pushed through the needle, the ACS came out into the vial. 100 µl of microsphere solution was dispensed into the vial. As the solution came out, the microspheres were sorbed by the collagen sponge. The method was termed "in situ seeding" and next evaluated for acute cell and microsphere delivery in vivo.

A.2. In Vivo Analysis of Acute Stem Cell Retention and Microsphere Distribution Following Injection into Discs in Combination with Collagen Sponge Materials:
1. Absorbable collagen sponge, same material as in A.1
2. Micro-Yucatan pig marrow-derived mesenchymal stem cells (MSCs). Expanded from frozen storage for 1 week and labeled with Europium colloid one day prior to in vivo use.
3. Scarlet microspheres, 15 µm (Molecular Probes)

Methods:

Two discs were injected with collagen plus Eu-labeled MSCs. For each disc, a thin strip of collagen sponge (approximately 3 cm long) was rolled between fingers and inserted into an 18 gauge thin-walled spinal needle.

40 million cells in 200 µl was combined with 1.2 ml of saline and drawn into a 1 cc syringe. The syringe was placed into the syringe gun and the needle attached.

The needle was placed into the disc center under fluoroscopic guidance. Approximately 200 µl of solution was dispensed from the syringe, half of which is the estimated hold up volume.

Two discs were injected with collagen plus scarlet microspheres. The microsphere solution (200 µl of microspheres+ 600 µl saline) and collagen sponge were delivered as described above.

After all four injections, the animal was sent to necropsy and the spine harvested. Discs injected with cells+collagen were collected for retention analysis. They were dissected with a small amount of bone attached, placed in BioPal vials, transected through the disc to expose the contents, dried in an oven, and sent to BioPal for Europium quantification. A control vial containing approximately 100 µl of cellular test article plus a non-injected disc was also analyzed for comparison. Standards of known cell numbers were also analyzed and used to prepare a standard curve of Eu dpm vs. cell number. Discs injected with microspheres+collagen were used for distribution analysis. They were dissected with some bone attached, bisected transversely, photographed, and imaged on the Xenogen IVIS instrument. Fluorescence imaging settings were cy5.5 filters, 0.5 s exposure, small binning, and f/stop 16.

Results:

Retention Analysis: Difficulties with the syringe gun and back pressure resulted in one of the collagen pieces during cell injection remaining in the needle. The piece was found in the hub after removing the needle from the syringe. The other cell/collagen injection was successful in placing the collagen into the disc, although back pressure caused the needle to pop off the syringe after dispensing 180 µl. Some leakage of solution from the needle hole was noticed in both injections.

Numbers of Eu-labeled MSCs in injected discs (n=2) and the control vial (Table 1) were calculated from measured Eu dpm values and the standard curve. For the disc in which cells and collagen were successfully delivered, there was good agreement between the number of cells delivered with collagen and the roughly equal volume in the control vial. Cells were also detected in the disc that the collagen did not make it into. The collagen recovered from the needle had an equal number of cells to the disc, indicating that the sponge did sorb cells during the injection.

TABLE 1

Measured and expected cells in collagen sponge injected samples

|  | Number of Cells | % Retention (% of control vial) |
| --- | --- | --- |
| Cells in first disc | $2.1 \times 10^6$ | 105% |
| Cells in second disc | $0.9 \times 10^6$ | 45% |
| Cells in recovered collagen in needle | $1.2 \times 10^6$ | 60% |
| Cells in control vial | $2.0 \times 10^6$ | |

Distribution Analysis: In both discs that were injected with microspheres and collagen sponge, the collagen was observed within the nucleus. The microspheres were detected in the nucleus associated with the collagen, but also separate from the collagen in nucleus and annulus. The collagen sponge removed from one of the discs shows the blue microspheres within half of the material. This is demonstration of the in situ seeding principal.

B. Conclusions

A solid carrier was evaluated in this study and determined to be a feasible vehicle for cell or microsphere delivery and acute retention in porcine discs. Collagen sponge could be delivered using a spinal needle, which offers the opportunity for a minimally invasive therapy.

Cells or microspheres can be delivered in combination with absorbable collagen sponge by a process of in situ seeding. The dry collagen is pushed from the needle into the disc by cell solution from a syringe gun, and the cells are sorbed into the collagen within the tissue.

Retention of cells was tested in the acute time frame, within 4 hours of injection. The solid carrier has potentially better retention than a fluid carrier because it is less likely to travel out through the needle track. They also offer the stem cells an immediate scaffold on which to adhere, which may enhance their therapeutic activity and response.

Example 2

In Vivo Assessment of Mesenchymal Stem Cell Delivery and Retention in Intervertebral Discs This study builds upon an acute study of cells and biomaterials delivered into porcine intervertebral discs discussed above in Example 1. The study presented in this Example compares the chronic delivery and retention of three approaches for cell delivery: (1) in a hydrogel, (2) in solution with a collagen sponge, (3) in solution without a biomaterial. Four week retention of adult, allogeneic mesenchymal stem cells delivered into porcine intervertebral discs was evaluated.

An overview of the results of this study show that injected MSCs were detected for each test article, with MSCs delivered with collagen sponge having the highest retention (49%, measured cells as a percentage of injected cells) followed by saline (17%), and hyaluronan gel (9%), respectively. Morphology of the injected MSCs indicates poor viability and no chondrogenesis. None of the test articles elicited an inflammatory response nor induced degeneration or damage.

In general it is concluded that a biomaterial carrier is not essential for MSC retention within the disc out to 4 weeks. However, retention is improved using a solid form carrier such as a sponge.

Study Design:

Healthy intervertebral discs in female pigs were injected with allogeneic, male BMSCs: 1) in saline, 2) in hyaluronan gel, 3) with a collagen sponge. Discs were collected at 4 weeks post-injection for MSC quantitation and histology.

A total of 8 female, domestic pigs that had never been bred were used. On the day of surgery, three lumbar discs in each animal were injected with a test article using an open, cutdown approach. Each animal received a single test article containing male porcine bone marrow stromal cells (BMSCs). A total of 4 test articles were studied, n=2 animals per TA (n=6 treated discs per TA). Four weeks after injection, animals were euthanized, and injected and uninjected discs were analyzed. To quantify cell retention, 3 discs per TA were excised and nucleic acid was isolated from the tissue. DNA analysis was performed to quantify the amount of Y chromosome present as a measure of injected male cells. Histopathology was performed on the remaining 3 discs per test article and compared to uninjected discs. Histology was done on spine segments containing discs of interest with a small amount of attached bone. Measures of exogenous cellularity were compared between test articles and correlated to histopathology results.

Materials:

Cells: BMSCs were isolated from adult, male porcine bone marrow and expanded in culture. The method of isolation was based on ficol gradient sedimentation and adherence to tissue culture plastic.

Biomaterial Vehicles:

1. Hyaluronan (MeroGel Injectable, Medtronic Xomed Surgical Products). This material is crosslinked and ready for use.

2. Absorbable collagen sponge (Integra LifeSciences).

Methods:

Surgeries: Female pigs were used so that injected, male cells could be tracked by a custom Y-chromosome assay. The surgeries were performed on multiple days. An open cutdown was used to access the lumbar spine.

1. Test Article 1: Cells in Saline

Cells were pelleted and resuspended in HBSS at a concentration of $25 \times 10^6$ cells/ml at time of surgery. The solution was drawn into a 1 cc syringe and the syringe attached to a modified Medtronic Everest screw-plunger syringe gun. A 25 gauge spinal needle was attached to the syringe and primed. Under fluoro, the needle was inserted into the disc center. 50 µl of cell suspension was injected per disc=$1.25 \times 10_6$ cells/disc. The needle was removed and the site examined for fluid leakage.

2. Test Article 2: Cells in Hyaluronan Gel

Cells were pelleted and resuspended in hyaluronan gel at time of surgery. Back and forth mixing between two 1 cc syringes was used. The final cell concentration was $25 \times 10^6$ cells/ml. Same injection procedure as for saline group except for volume injected. 100 µl of cell suspension was injected per disc=$2.5 \times 10^6$ cells/disc.

3. Test Article 3: Cells with Collagen Sponge

Prior to day of surgery, collagen sponge strips (approximately 2 mm wide×40 mm long) were rolled between gloved fingers and threaded inside 18 gauge thin walled spinal needles, one per needle. The pre-filled needles were sterilized by ethylene oxide (EtO). On the day of surgery, cells were pelleted and resuspended in HBSS at a concentration of $22.5 \times 10^6$ cells/ml. The solution was drawn into a 1 cc syringe and the syringe attached to a modified MDT Everest screw-plunger syringe gun. An 18 gauge needle pre-filled with collagen was attached to the syringe, but not primed (priming would push the collagen out). Under fluoro, the needle was inserted into the disc center. 250 µl of cell suspension was ejected from the syringe. The hold-up volume in the needle is approximately 150 µl, so roughly 100 µl plus the collagen sponge was injected≈$2.25 \times 10^6$ cells/disc. The needle was rotated and removed.

4. Sample Analysis

Four weeks after injection, animals were euthanized and spines excised. For each spine, soft tissues were stripped off and the posterior elements were removed. Discs for histology were dissected with a small portion of vertebral body attached. The tissues were fixed and decalcified for several weeks and then trimmed sagitally into approximately 15-20 pieces. Five pieces were selected for sectioning and staining: one from the approximate center, two adjacent to it, and two from the lateral margins. Serial sections were cut 6 microns thick and stained with H&E, safranin-O, and trichrome stains. The sections were analyzed for presence of the injected cells and/or material and changes to cellularity and matrix architecture compared to non-injected discs.

Discs for DNA analysis were bisected transversely and photographed. Nucleus and annulus were dissected and snap frozen separately. Total nucleic acid (TNA) was isolated from tissues using homogenization and the Epicentre MasterPure DNA isolation kit (Catalog #MCD85201). TNA was split into two aliquots, one for DNA purification and one for RNA purification (not used in this study). Purified DNA was used in a custom SRY gene assay to detect amount of male DNA (from injected cells) by real-time PCR. A standard curve of genomic DNA was used to allow absolute quantitation of Y chromosome present.

Results:

Cell Retention: Table 2 reports the numbers of injected cells in nucleus and annulus samples for each test article-treated disc and for untreated discs. The SRY gene assay has a lower limit of detection of approximately 10,000 cells. Samples with measured numbers less than 10,000 were rounded down to zero. With one exception, untreated discs did not contain SRY gene positive cells above the limit of detection. The exception may be because of sample contamination at the time of collection.

Discs injected with cells plus collagen sponge had the greatest numbers of cells at 4 weeks post-injection. Greater than 500,000 stem cells were measured in the nucleus of each of the three treated discs with far fewer in the annulus.

These data reveal high variability in the number of stem cells in treated discs at 4 weeks. One disc treated with cells in saline had no detectable cells in the nucleus but some in the annulus. These results may be due to complications or errors during injection.

TABLE 2

Numbers of injected stem cells in nucleus and annulus samples as measured by Y chromosome assay.

| | Saline Animal 332221 | | Saline Animal 332220 | | Hyaluronan Animal 332223 | | Hyaluronan Animal 332217 | | Collagen Animal 332219 | | Collagen Animal 332224 | |
|---|---|---|---|---|---|---|---|---|---|---|---|---|
| | NP | AF | NP | AF | NP | AF | NP | AF | NP | AF | NP | AF |
| SL6 (T13L1) | 0* | 0* | | | 0* | 0* | | | 0* | 0* | 0* | 0* |
| SL5 (L1L2) | | | 0* | 0* | | | 0* | 0* | | | | |
| SL4 (L2L3) | 61,201 | 38,766 | | | 74,285 | 9721 | | | 766,259 | 29,589 | 587,204 | 0 |
| SL3 (L3L4) | | | 0 | 115,674 | | | 339,699 | 18,449 | | | | |
| SL2 (L4L5) | 399,834 | 0 | | | 249,608 | 0 | | | 1,760,501 | 20,096 | 0* | 0* |

TABLE 2-continued

Numbers of injected stem cells in nucleus and annulus samples as measured by Y chromosome assay.

| | Saline Animal 332221 | | Saline Animal 332220 | | Hyaluronan Animal 332223 | | Hyaluronan Animal 332217 | | Collagen Animal 332219 | | Collagen Animal 332224 | |
|---|---|---|---|---|---|---|---|---|---|---|---|---|
| | NP | AF | NP | AF | NP | AF | NP | AF | NP | AF | NP | AF |
| SL1 (L5L6) | | | 0* | 0* | | | 0* | 0* | | | | |

Assay has a lower limit of sensitivity of approximately 10,000 cells;
*= untreated;
NP = nucleus pulposus;
AF = annulus fibrosis Table 3 reports the mean number of cells in the whole disc (nucleus+annulus) for each test article. For cells plus collagen, the mean value measured represents 49% of the estimated amount injected. Other test articles had a lower percentage retention: 17% for cells in saline, and 9% for cells in hyaluronan gel.

TABLE 3

Mean total number and percent retention in cell injected discs

| | Mean total # measured stem cells per disc | Estimated # injected stem cells per disc | Mean % Retention |
|---|---|---|---|
| Saline | 210,000 ± 170,000 | $1.25 \times 10^6$ | 17 |
| Hyaluronan | 230,000 ± 140,000 | $2.5 \times 10^6$ | 9 |
| Collagen | 1,100,000 ± 640,000 | $2.25 \times 10^6$ | 49 |

Histology and Gross Observations: Gross observations indicate that none of the test articles or procedures caused significant damage or degeneration. Aside from injected test article in some discs, the nucleus of all treated discs looked similar to untreated discs in color and consistency. No significant changes were noted to annulus structure. No treated discs contained blood, pus, or signs of inflammation or infection. Most, however, had some tissue hypertrophy and pallor outside the annulus at the site of needle penetration.

Exogenous stem cells or material were observed in at least one disc from all four test articles by histological examination as determined by comparison to normal discs. Disc morphology across all treatments was similar to non-treated discs. None of the test articles adversely affected disc height, annulus structure, nucleus proteoglycan content, extra-discal cellularity, or endplate morphology.

Matter within the disc was identified as test article because of its distinct appearance compared to the normal nucleus morphology. MSCs in the cells/collagen disc looked more like those in the saline group than the hyaluronan group. The cells occupied a larger area of the nucleus than the MSCs in saline or hyaluronan, and they were better mixed with endogenous proteoglycan matrix. The collagen sponge was not evident based on staining and may have already degraded.

Discussion:

Porcine MSCs were detected within the nucleus pulposus of discs four weeks after injection. A biomaterial carrier was not required for cell retention. However, retention was improved using a solid form carrier. The best retention occurred by co-administering cells in saline with a collagen sponge. Based on earlier experiments, the sponge presumably aids retention by sorbing the cells in situ and reducing the amount that exudes out of the damaged annulus after injection. Cell retention was not improved using a viscous gel vehicle in place of a saline suspension.

While much of the present disclosure has focused on therapeutic aspects of delivering particles to a subject, it will be understood that the devices, systems and methods described herein may be employed to for any suitable purpose, including (i) studying the effects of particles, such as cells or particles containing drugs or biomolecules, on a subject, (ii) studying techniques for injecting particles into a subject, which studies may include live or deceased subjects or portions thereof or models of subjects or portions thereof, (iii) or the like. Some of such studies may aid in developing therapeutic applications or procedures.

The headings used herein are for the purpose of convenience and clarity and should not be interpreted as being limiting. By way of example, discussion of systems and devices, or components thereof, under the heading "Methods" are discussion of systems and devices, or components thereof, contemplated herein. By way of further example, the methods described under the heading "Systems" are discussion of methods contemplated herein.

Thus, embodiments of PARTICLE DELIVERY are disclosed. One skilled in the art will appreciate that the arrays, compositions, kits and methods described herein can be practiced with embodiments other than those disclosed. The disclosed embodiments are presented for purposes of illustration and not limitation.

What is claimed is:

1. A system for delivering particles to a patient; the system comprising:
    an infusion device having a reservoir configured to house the particles;
    a delivery element having a proximal end, a distal end, a delivery region between the proximal end and the distal end, and a lumen extending from the proximal end to the delivery region, the delivery element being operably couplable to the infusion device such that particles from the reservoir are deliverable via the delivery region of the delivery element, the delivery element comprises a stop feature between the proximal and distal end to prevent a polymeric carrier from being inserted proximally in the lumen beyond the stop feature;
    a polymeric carrier in the form of a compressed sponge slidably disposed in the lumen such that the carrier is spaced apart from the proximal and distal ends of the delivery element, wherein delivery of the particles from the reservoir via the delivery region of the delivery element causes the polymeric carrier to exit to the delivery region of the delivery element;
wherein the particles comprise cells, the cells having a concentration between about $1 \times 10^7$ cells/mL and about $1 \times 10^9$ cells/mL.

2. The system of claim 1, further comprising the particles.

3. The system of claim 1, wherein the particles comprise microspheres.

4. The system of claim 1, wherein the particles are in a fluid suspension.

5. The system of claim 1, wherein the polymeric carrier is resiliently compressible and is water-swellable.

6. The system of claim 5, wherein the polymeric carrier has a water absorption of 100% or more.

7. The system of claim 1, wherein the carrier comprises collagen.

8. The system of claim 1, wherein the carrier consists essentially of collagen.

9. The system of claim 1, wherein the carrier comprises a collagen sponge configured to serve as a scaffold for cell growth, the carrier having a therapeutic agent incorporated therein configured to promote cell growth.

10. The system of claim 1, wherein the polymeric carrier in the form of the compressed sponge is rolled and slidably disposed in the lumen.

* * * * *